United States Patent [19]

Carle

[11] 4,055,087
[45] Oct. 25, 1977

[54] AQUATIC-LIFE DEPLETION-SAMPLING DEVICE AND TECHNIQUE

[76] Inventor: Frank Louis Carle, 146 Mount View Road, Warren, N.J. 07060

[21] Appl. No.: 746,083

[22] Filed: Nov. 30, 1976

[51] Int. Cl.$^2$ .............................................. G01N 1/12
[52] U.S. Cl. ................................... 73/421 R; 37/57; 43/4; 73/425.2
[58] Field of Search ................ 73/421 R, 425, 425.2, 73/425.4, 421 B; 43/7, 4, 100, 103; 37/54–57

[56] References Cited

U.S. PATENT DOCUMENTS

| 82,490 | 9/1868 | Cartwright | 43/100 |
| 1,474,731 | 11/1923 | Podolsky | 43/103 |
| 3,003,278 | 10/1961 | Armentrout | 43/103 |
| 3,811,325 | 5/1974 | Carter | 73/425.4 R |
| 3,862,502 | 1/1975 | Young | 37/55 |
| 3,894,711 | 7/1975 | Nezat | 37/57 |

FOREIGN PATENT DOCUMENTS

| 244,704 | 11/1967 | U.S.S.R. | 73/425.2 |

Primary Examiner—Daniel M. Yasich

[57] ABSTRACT

In a preferred embodiment, a cylindrically-shaped forwardly-screened vessel having an open lower end and an open or netted upper end, and at a rearward wall of the vessel there being a curved collector plate having centrally thereof an outlet port to which is anchored a narrowing sock tapering to a narrow opening including a sample bag-fastening device together with a detachable filter-sample bag of typically cloth, and the cylindrical walls at the open bottom having a sharpened edge facilitating twisting rotatably to and fro into a sea, lake, river, or stream bottom to be sampled, or having, in the case of impermeable substrate, an attachable foam ring, prior to agitation. Upon agitation, the tidal, stream or artificially-induced current flows through the screen forwardly portion carrying plant and animal life rearwardly through the outlet port through the tapering sock into the filter-sample bag which retains specimens for subsequent identification or counting, or both. Replacing sampling bags, and sampling is repeated several times for the same location before moving the vessel.

12 Claims, 6 Drawing Figures

AQUATIC-LIFE DEPLETION-SAMPLING DEVICE AND TECHNIQUE

This invention relates to an aquatic-life depletion-sampling device & technique.

BACKGROUND TO THE INVENTION

Prior to the present invention, the present inventor being a specialist in the field of aquatic-life sampling technology, became aware of the less-than-accurate and less-than-controlled conditions under which prior sampling devices and techniques operated in cumbersome attempts to arrive at some semblance of reliable information as to estimation of animal life of small and/or microscopic sizes. Typical of such was a gadget in the nature of a mere funnel-like structure held in the hand, extending beneath the water slightly above the bottom thereafter agitated with a booted-foot or with a gloved-hand upstream of the funnel-like structure, in hopes of catching a representative sample of aquatic animal life within the funnel netting attached to the rear thereof for retaining the funneled matter successfully captured.

SUMMARY OF THE INVENTION

Accordingly, objects of the present invention include the overcoming and/or avoiding of difficulties and problems of the types described above, together with making substantial advances in stucture and technique.

Another object is to obtain a device portable in nature which is substantially accurate in area sampled and which enables accurate and precise estimation of all plant and animal life from a stream, lake, or sea bottom from within the sampled area.

Another object is to obtain an improved aquatic life sampler for novelly anchoring within a stream, river, lake, or sea bottom for an area to be sampled.

Another object is to obtain an improved aquatic life sampler which prevents emigration out of and immigration into the sample area of aquatic life.

Another object is to develop an improved technique or process of sampling aquatic life for estimation thereof.

Another object is to obtain an improved aquatic life sampler for novelly anchoring within a stream, river, lake, or sea bottom for an area to be sampled, making use of artificially-induced flow of water.

Other objects become apparent from the preceding and following disclosure.

One or more objects are obtained by the following illustrative embodiments.

Broadly the invention may be defined as a novel vessel having an open bottom as well as a top opening at least large enough for inserting typically a gloved hand, or otherwise substituting an equivalent method or apparatus for agitation, such as a foot-compressing air-propelled water-pump or the like for inducing artificial flow and/or agitation, in order to agitate the area circumscribed and substantially enclosed by the vessel. There is a fine mesh screen on one side, i.e. a forward portion of the circumscribing walls in order that when placed in an upstream direction water flow into the vessel through the screen sweeps enclosed plant and animal entities suspended in agitated water rearwardly against the rearwardly-located portion of the circumscribing walls, through an outlet port therein into an outside-attached funnel element onward rearwardly through an outlet thereof into an attached open-mouthed sample-collecting bag of a waterporous filter-bag retainable of plant and animal life.

In various preferred embodiments, the vessel is substantially cylindrically shaped, and the funnel element is tapered from the enlarged inlet thereof to a narrowed outlet thereof where the attaching or bag-fastening mechanism is a ring-shaped coil-spring for constricting tightly about an upper mouth portion of the sample bag holding it firmly onto the narrowed portion of the funnel element. Alternately a pivoted clamping ring represents another embodiment, which when flipped-up on-top of the bag neck anchors the bag, and becomes preferably latched in the flipped-up position. Also, the base of the cylindrical vessel has a circular structure forming a ring with a downwardly-directed cutting edge such that the vessel when worked to and fro clockwise and counterclockwise cuts its way into the bottom of the stream, river, lake, or sea, avoiding tilting of the vessel. Thereby it cleanly and firmly circumscribes the area to be sampled, preventing emigration or immigration of aquatic life to and from the area to be sampled by agitation of the circumscribed bottom or bed. In the event of an impervious bottom, a detachable foam ring slides onto the bottom of the vessel, to seal-off the sample area.

As would be the case with a cylindrical vessel, the rearwardly-located portion of the circumscribing walls is concave in at least the horizontal plane — this facilitating the water-suspended plant and animal life to be swept by upstream or artificial currents (i.e. the use of compressed air for example) flowing through the forward netting or screen, centrally into the outlet port onwardly through the funnel element. At the outlet of the funnel element, there is a preferred latching mechanism for attaching the funnel-outlet portion to an upper edge of the vessel during each of transport thereof, and during attaching and removing of the sample-bag to the narrowed outlet end, thereby preventing the escape of aquatic life.

The method includes placing an open-bottomed circumscribing-walled vessel downwardly onto a stream, river, lake or sea bottom with a netting or screen portion of the forward wall of the vessel facing an upstream direction in streams and rivers, for example, and with an outlet port thereof and an attached funnel structure and bag mounted thereon in a downstream direction; thereafter there is agitating an entire circumscribed area of the stream, river, lake, or sea bottom; thereafter, manual manipulation manually facilitates material adhered to walls to become loosened and induced to flow onwardly rearwardly into the sample bag. Thereafter, the bag is removed and closed for later identification and or counting of entities of the contents. Then the entire procedure of placing another bag onto the funnel device without disturbing the vessel from its initial location, is repeated an additional one or more times, each time labeling the bag removed as to the location and as to which number of sampling in series that bag represents, normally about three consecutive samples being obtained from a single setting of the vessel at a particular location within the stream, river, lake, or sea, etc., bottom.

While various methods of assembling the vessel and the funnel structure may be utilized as might be conventional or otherwise desired, the funnel structure should be well sealed to the outlet port of the vessel to prevent loss of sample during its passage therethrough, particularly when tapping and squeezing the funnel — typically of flexible netted material, in the advancing of clinging entities therewithin, to obtain the complete sample within the sample bag in-so-far as is reasonably possible. Typically and preferably the vessel is made out of light metal or plastic.

The invention may be better understood by making reference to the following Figures.

THE FIGURES

DETAILED DESCRIPTION OF THE INVENTION

Figure 1:
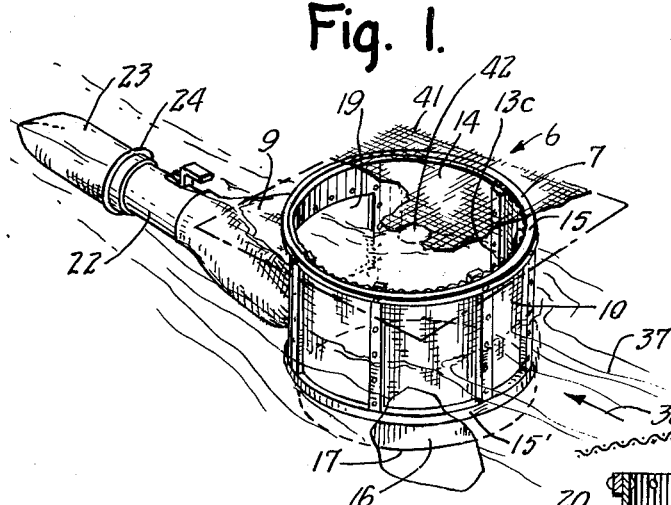
FIG. 1 illustrates a front top perspective view of a preferred embodiment of the invention, operatively placed in a cut-in settled position and state into a stream bed facing the upstream oncoming water, with the funnel element in the down-stream position with bag attached thereto.
Figure 2:
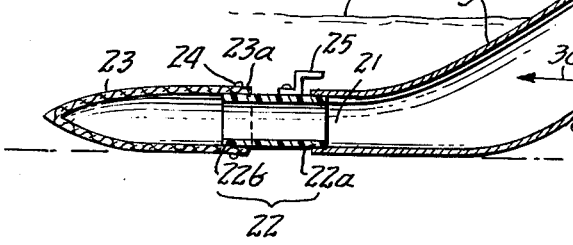
FIG. 2 illustrates a side cross-sectional view of the embodiment of FIG. 1, in a cut-in settled position and state into a stream bed facing the upstream oncoming water.
Figure 3:
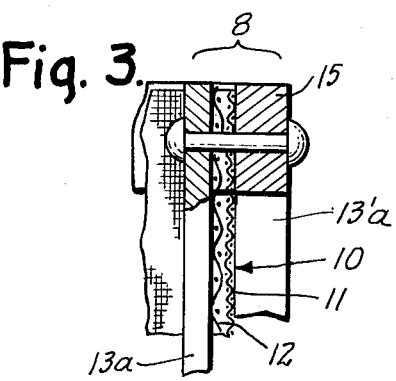
FIG. 3 illustrates an in-part view of the circumscribed portion 8 of FIG. 2, in side cross-sectional view, in an enlarged view thereof.

While the forward or front portion has been referred to as fine mesh screen, or as netting, in fact in a preferred embodiment there is used in the "sense", a fine netting 11 and a larger support screen — i.e., larger mesh, jointly making up the screen 10, there being screen supports 13a, 13b, 13c, etc., fastened against side supports such as 13'a, supporting the screen and netting therebetween, as seen in FIGS. 1, 2, and 3.

Figure 6:
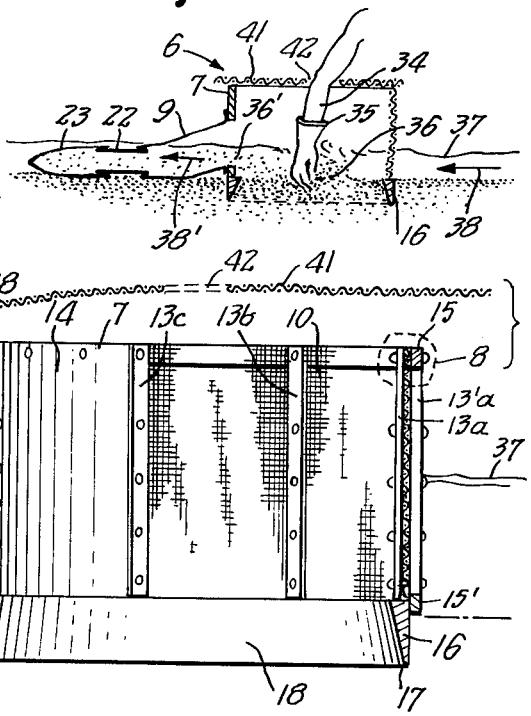
FIG. 6 illustrates the embodiment of FIG. 1, illustrating agitation of the substrate, in a side cross-sectional view of the vessel in settled state within the stream.
Figure 4:
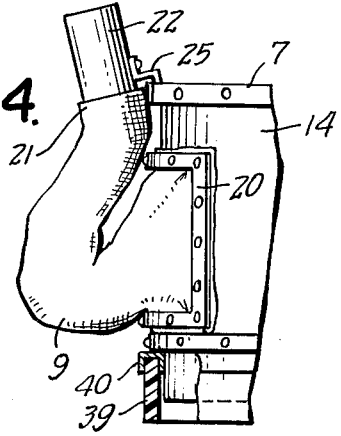
FIG. 4 illustrates an in-part view of the same embodiment in side view thereof, with the outlet end of the funnel element attached to an upper edge of the circumscribing wall of the vessel, and also showing the detachable foam ring.

The aquatic-life depletion-sampler device 6 includes the area-defining vessel structure 7 having the screen 10 as the front walls and the backing plate 14 as the rearwardly-located circumscribing portion of the back wall, and with or without netting 41 having an opening 42. The above-described screen front or forward circumscribing portion is typically identified as portion 8 of FIG. 2, shown in enlarged view in FIG. 3, including an upper ring 15 and a lower ring 16 of FIGS. 1 and 2, with the cutting edge 17 encircling all the bottom to be agitated. In the centered rear face of plate 14 is the outlet port 19 continuous with through-space of the funnel element 9, fastened by bolt elements 20 to the plate 14. Water 37 flowing from the forward (upstream) direction 38 passes into the vessel 7 through the screen 10 and travels along the funnel element space in direction 38' through outlet 21 into the bag-attaching tubular element at proximal end 22a onto which the bag mouth 23a of bag 23 is constricted and held by ring coilspring 24 at tubular element distal end 22b of the tubular element 22; such tubular element may be considered an integral part of the funnel element 9, for all practical purposes and need not necessarily be a separate element. The agitation takes place within the space 18, surrounded by the lower ring 16 knifing into the bottom; however, if an imperveous bottom/substrate, a foam ring 39 is detachably mounted by a sealing ring (retainer ring 40, to the lower ring 16. Attaching element 25 serves to hang the distal end of the funnel element upon an upper edge/ring 15 of the vessel 7, advantageous to so do during the carrying of the device, as well as especially during the mounting and dismounting of sample bag to prevent the escape of aquatic life, best illustrated in the FIG. 4 view. The cutting edge structure 16 is mounted at a base of the lower ring 15'. FIG. 6 well illustrates these parts diagrammatically, together with illustrating the technique of agitation within the defined and enclosed volume for the specific area of bottom circumscribed by the cutting edge structure 16, the person's arm 34 wearing glove 35 causing matter 36 to be agitated to thereby suspend plant and animal entities, to be thereafter carried by the natural or induced current or water-flow, into and through the funnel structure element.

Figure 5:
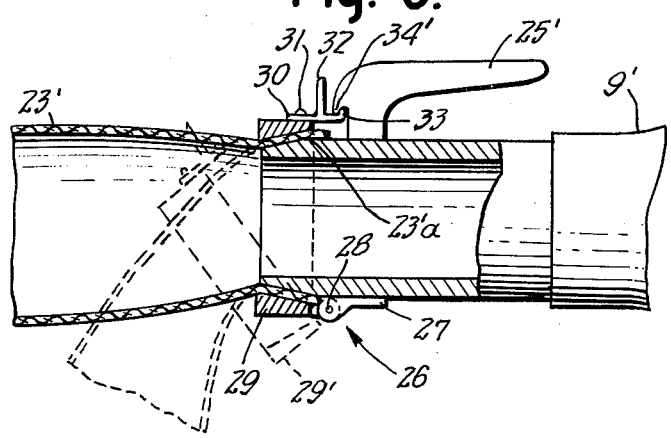
FIG. 5 illustrates an alternate embodiment, in an in-part side cut-away view thereof, illustrating an alternate bag-attaching mechanism.

FIG. 5 illustrates an alternate embodiment showing the bag-securing mechanism to be a pivoted ring 29 pivotal to the position 29' on pivot pin 28, with fastener 30 held thereon by pin 31, and engaged with over-hang latch 34', and releasable from the latch by pressing the handle 32 toward the attaching element 35 to thereby disengage the fastener 33. Other parts are identified by corresponding prior numerals, as 9' for the funnel element of this differing embodiment, having novel bag-fastening mechanism 26 by which the bag 23' becomes constricted onto the distal end at the bag-mouth 23'a.

Typically, the backing plate, the cutting edge structure 16, and the screen retainers are made of 0.08 cm galvanized sheet metal. The upper and lower (bottom) rings are about 205 cm in length and about 1.27 cm square. The total height is about 38.1 cm. Inside circumference is about 204.6 cm, and inside diameter is about 65.1 cm. The coarse support screen is typically galvanized wire having 1.6 meshes per cm. The fine front mesh or net is typically Nylon screening with 17 meshes per cm, and the funnel is about 19 by 40 and has a length 35 cm. A band of foam rubber preferably seals the interface between the collecting net and the backing plate.

It is to be understood that the above dimensions and materials for one preferred embodiment are not intended to be limiting narrowly in so far as scope of the invention is concerned, while such are intended to illustrate the spirit of the invention as described. Accordingly, it is within the scope and spirit of the invention to make such variations and modifications and substitutions as would be apparent to a person of ordinary skill.

Note, that in a preferred procedure, the bags are labeled in the order of sequence of the samples consecutively taken from a common area, before moving the device. Thereafter, estimates are calculated conventionally, or by any new approach, to arrive at the final determination.

I claim:

1. An aquatic life sampling device comprising in combination: a vessel structure having substantially upright circumscribing walls forming a substantially downwardly-facing open bottom and forming an upper-opening in an upper portion thereof, an upper-opening closure means for normally closing the upper-opening and for intermittently gaining access to enclosed space within the circumscribing walls, at least forwardly-located portions of the circumscribing walls comprising fine meshed screen and rearwardly-located portions of the circumscribing walls including a barrier plate having a through-passage outlet port formed therein, a funnel element having a forward structure thereof forming an enlarged inlet and a rearward structure thereof forming a narrowed outlet, the forward structure being attached and sealed to said rearwardly-located portion with said enlarged inlet being aligned in flow-communication with said outlet port, and bag-fastening means for mounting an open-mouthed porous sample bag on said rearward structure in flow communication with said narrowed outlet into an open mouth of the mounted sample bag.

2. A aquatic life sampling device of claim 1, in which said rearwardly-located portion of the circumscribing walls is concave in at least a horizontal plane, said outlet port being substantially centered within a concave portion of said rearwardly-located portion of the circumscribing walls.

3. An aquatic life sampling device of claim 2, including a substantially circular structure forming a downwardly-directed cutting edge, mounted on and along a bottom of said circumscribing walls with the circular structure substantially circumscribing said open bottom.

4. An aquatic life sampling device of claim 3, in which said vessel structure is substantially cylindrical in shape.

5. An aquatic life sampling device of claim 4, in which said funnel element tapers from said enlarged inlet to said narrowed outlet.

6. An aquatic life sampling device of claim 5, including a latching means for intermittently attaching the rearward structure to an upper edge of said vessel structure.

7. An aquatic life sampling device of claim 1, including a latching means for intermittently attaching the rearward structure to an upper edge of said vessel structure.

8. An aquatic life sampling device of claim 1, including a substantially circular structure forming a downwardly-directed cutting edge, mounted on and along a bottom of said circumscribing walls with the circular structure substantially circumscribing said open bottom.

9. An aquatic life sampling device of claim 1, in which said vessel structure is substantially cylindrical in shape.

10. An aquatic life sampling device of claim 1, in which said funnel element tapers from said enlarged inlet to said narrowed outlet.

11. A method for aquatic life depletion sampling comprising in combination: placing a mouth of an open-bottom vessel having a lateral screened-wall and an oppositely-positioned rearward outlet port and attached collecting funnel element and sampler bag porous to water, into mouth-contact substantially sealably with a bottom surface within a body of water of a water-test area to thereby accurately circumscribe and substantially enclose therein a predetermined area of the bottom surface, and facing the lateral screened-wall toward upstream direction within said water-test area such that current brings water through the screened-wall into thereby substantially enclosed space above the predetermined area of the bottom surface, to sweep onwardly through the rearward outlet port into the collecting funnel element and sampler bag attached thereto, and thereafter agitating said bottom surface of said predetermined area sufficiently to cause plant and animal small entities to become suspended within environmental water within the vessel, whereby the entities are swept into the sampler bag.

12. A method of claim 11, including removing the bag after the suspended entities have been flushed into the bag, and replacing the bag with a second empty bag, and repeating the agitation from the same enclosed area, and thereafter removing the second bag after the suspended entities have been flushed into the bag.

* * * * *